United States Patent [19]

Heinemann et al.

[11] Patent Number: 5,240,926
[45] Date of Patent: Aug. 31, 1993

[54] SUBSTITUTED PYRIDYLTRIAZINES

[75] Inventors: Ulrich Heinemann, Leichlingen; Dietmar Kuhnt, Leverkusen; Heinz-Wilhelm Dehne, Monheim; Stefan Dutzmann, Hilden, all of Fed. Rep. of Germany

[73] Assignee: Bayer Aktiengesellschaft, Leverkusen, Fed. Rep. of Germany

[21] Appl. No.: 934,139

[22] Filed: Aug. 21, 1992

[30] Foreign Application Priority Data

Aug. 30, 1991 [DE] Fed. Rep. of Germany ....... 4128789

[51] Int. Cl.$^5$ .................... C07D 401/04; A01N 43/66
[52] U.S. Cl. .................... 514/241; 514/219; 514/180; 514/216
[58] Field of Search .............. 544/180, 216, 219; 514/241

[56] References Cited

U.S. PATENT DOCUMENTS 4,873,248 10/1989 Katoh et al. .................... 514/269

FOREIGN PATENT DOCUMENTS 0270362 12/1987 European Pat. Off. .
91/07399 5/1991 PCT Int'l Appl. .

OTHER PUBLICATIONS

Tetrahedron Letters 12, 1393–1396 (1981), Figeys et al.

Primary Examiner—John M. Ford
Attorney, Agent, or Firm—Sprung Horn Kramer & Woods

[57] ABSTRACT

New substituted pyridyltriazines of the formula (I)

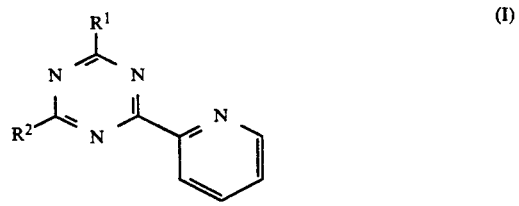

in which $R^1$ and $R^2$ have the meanings given in the description, and their use for combating pests.

The compounds can be prepared by analogous processes, for example by reacting pyridylamidine hydrochloride with suitable methyl imidates or with suitable benzene-isothiocyanates, or by desulphurising mercapto-substituted pyridyltriazines or by reacting them with alcohols. The mercapto-substituted compounds are also new and can be prepared by analogous processes.

6 Claims, No Drawings

SUBSTITUTED PYRIDYLTRIAZINES

The invention relates to new substituted pyridyltriazines, to a plurality of processes for their preparation, to their use as pesticides, and to novel intermediates.

It is known that certain substituted pyridylpyrimidines such as, for example, the compound 2-(6-methyl-2-pyridyl)-4-(2-methylphenyl)-pyrimidine or the compound 2-(6-methyl-2-pyridyl)-4-phenyl-6-hydroxypyrimidine or the compound 2-(6-methyl-2-pyridyl)-4-phenyl-6-methoxypyrimidine, have fungicidal properties (cf., for example, EP 270,362).

However, the activity of these previously known compounds is not entirely satisfactory in all fields of application, in particular when low amounts and concentrations are used.

New substituted pyridyltriazines of the general formula (I)

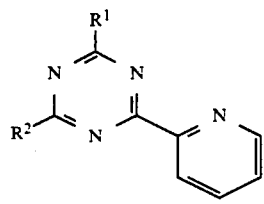

in which
$R^1$ represents hydrogen, alkyl, alkoxy or alkylthio and
$R^2$ represents optionally substituted phenyl,
have been found.

Furthermore, it has been found that the new substituted pyridyltriazines of the general formula (I)

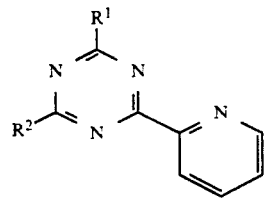

in which
$R^1$ represents hydrogen, alkyl, alkoxy or alkylthio and
$R^2$ represents optionally substituted phenyl,
are obtained when a) in the event that $R^1$ represents alkyl, pyridylamidine or its acid addition salts of the formula (II)

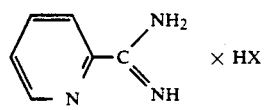

in which X represents an anion of an inorganic acid is reacted with imidates of the formula (III)

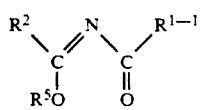

in which
$R^{1-1}$ represents alkyl, $R^2$ has the abovementioned meaning and
$R^5$ represents alkyl or aryl, if appropriate in the presence of a diluent and if appropriate in the presents of a reaction auxiliary, or when b) in the event that $R^1$ represents hydrogen, mercaptotriazinylpyridines of the formula (IV)

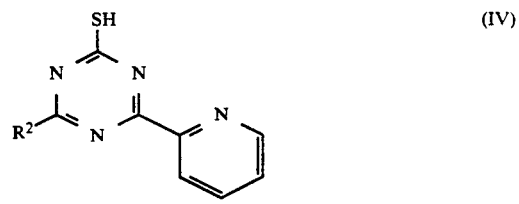

in which $R^2$ has the abovementioned meaning, are desulphurised with Raney nickel, if appropriate in the presence of a diluent, or c) in the event that $R^1$ represents alkylthio, the compounds of the formula (IV) are reacted with alkylating agents of the formula (V)

$$R^3-E \qquad (V)$$

in which
$R^3$ represents alkyl and
E represents an electron-attracting leaving group,
if appropriate in the presence of a diluent and if appropriate in the presence of a reaction auxiliary, or when d) in the event that $R^1$ represents alkoxy, the alkylthio-triazinylpyridines of the formula (Ia)

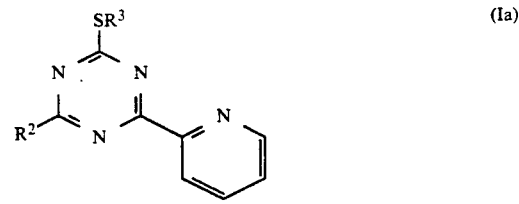

in which
$R^3$ represents alkyl and
$R^2$ has the abovementioned meaning,
which can be obtained with the aid of process (c) according to the invention, are reacted with alcohols of the formula (VI)

$$R^4-OH \qquad (VI)$$

in which $R^4$ represents alkyl, if appropriate in the presence of a diluent and if appropriate in the presence of a reaction auxiliary.

The compounds of the formula (IV) can also exist in the tautomeric thioketo form.

Finally, it has been found that the new substituted pyridyltriazines of the general formula (I) have a good biological, mainly fungicidal, activity.

Surprisingly, the substituted pyridyltriazines of the general formula (I) according to the invention show a markedly better fungicidal activity than the substituted pyridylpyrimidines known from the prior art such as, for example, the compound 2-(6-methyl-2-pyridyl)-4-(2-methylphenyl)-pyrimidine or the compound 2-(6-methyl-2-pyridyl)-4-phenyl-6-hydroxy-pyrimidine or the compound 2-(6-methyl-2-pyridyl)-4-phenyl-6-methoxypyrimidine, which are similar compounds chemically and from the point of view of their action.

Formula (I) provides a general definition of the substituted pyridyltriazines according to the invention. Preferred compounds of the formula (I) are those in which $R^1$ represents hydrogen, straight-chain or branched alkyl having 1 to 6 carbon atoms, straight-chain or branched alkoxy having 1 to 6 carbon atoms, or straight-chain or branched alkylthio having 1 to 6 carbon atoms, and $R^2$ represents phenyl which is optionally monosubstituted or polysubstituted by identical or different substituents, suitable substituents being: halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, or phenyl which is optionally monosubstituted or polysubstituted by identical or different substituents from the series comprising halogen and/or straight-chain or branched alkyl having 1 to 4 carbon atoms.

Particularly preferred compounds of the formula (I) are those in which $R^1$ represents hydrogen, straight-chain or branched alkyl having 1 to 4 carbon atoms, straight-chain or branched alkoxy having 1 to 4 carbon atoms or straight-chain or branched alkylthio having 1 to 4 carbon atoms, and $R^2$ represents phenyl which is optionally monosubstituted to trisubstituted by identical or different substituents, suitable substituents being: fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl or phenyl which is optionally monosubstituted to trisubstituted by identical or different substituents from the series comprising fluorine, chlorine, bromine, methyl and/or ethyl.

Very particularly preferred compounds of the formula (I) are those in which $R^1$ represents hydrogen, methyl, ethyl, n- or i-propyl, n-, i-, s- or t-butyl, methoxy, ethoxy, methylthio or ethylthio, and $R^2$ represents phenyl which is optionally monosubstituted or disubstituted by identical or different substituents, suitable substituents being: fluorine, chlorine, bromine, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy or trifluoromethylthio.

Individual substituted pyridyltriazines of the general formula (I) which may be mentioned in addition to the compounds mentioned in the Preparation Examples are the following:

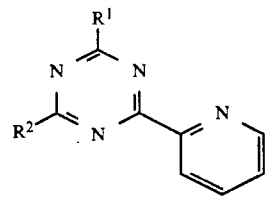

(I)

| $R^1$ | $R^2$ |
|---|---|
| t-$C_4H_9$ |  |
| t-$C_4H_9$ |  |
| n-$C_4H_9$ | 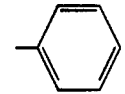 |
| i-$C_3H_7$ | 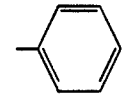 |
| i-$C_3H_7$ |  |
| n-$C_3H_7$ |  |
| $C_2H_5$ |  |
| $C_2H_5$ | 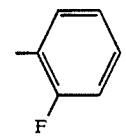 |
| H |  |
| H | 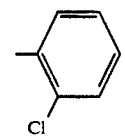 |
| H | 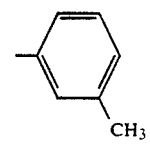 |

-continued
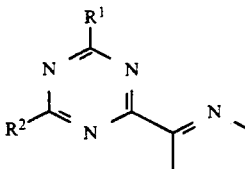  (I)
| R¹ | R² |
|---|---|
| —S—CH₃ | 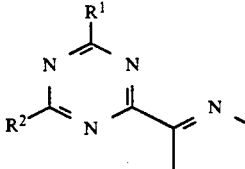 |
| —S—CH₃ | 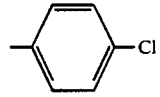 |
| C₂H₅ | 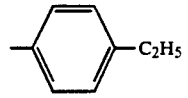 |
| C₂H₅ | 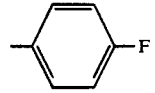 |
| CH₃ | 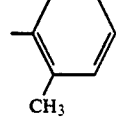 |
| H | 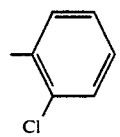 |
| H | 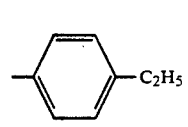 |
| CH₃ | 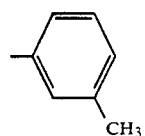 |
| CH₃ | 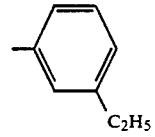 |
| —O—C₂H₅ | 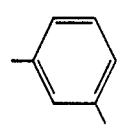 |
-continued
  (I)
| R¹ | R² |
|---|---|
| —S—CH₃ | 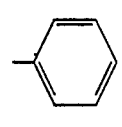 |
| C₂H₅ | 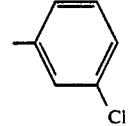 |
| C₂H₅ | 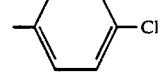 |
| C₂H₅ | 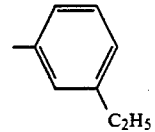 |
| —S—C₂H₅ | 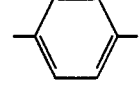 |
| —S—C₂H₅ |  |
| —O—CH₃ | 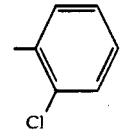 |
| —O—CH₃ | 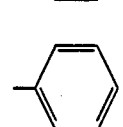 |
| —S—CH₃ | 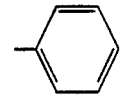 |
| —S—C₂H₅ | 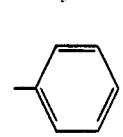 |

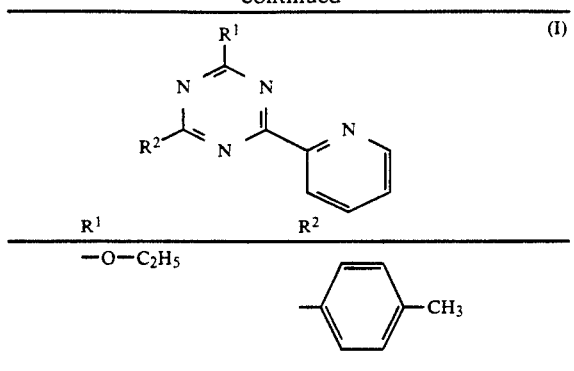

| R¹ | R² |
|---|---|
| —O—C₂H₅ | -⌬-CH₃ (p-tolyl) |

If, for example, 2-pyridylamidine hydrochloride and methyl N-acetyl-benzeneimidocarboxylate are used as starting compounds, the course of the reaction of process (a) according to the invention can be represented by the following equation:

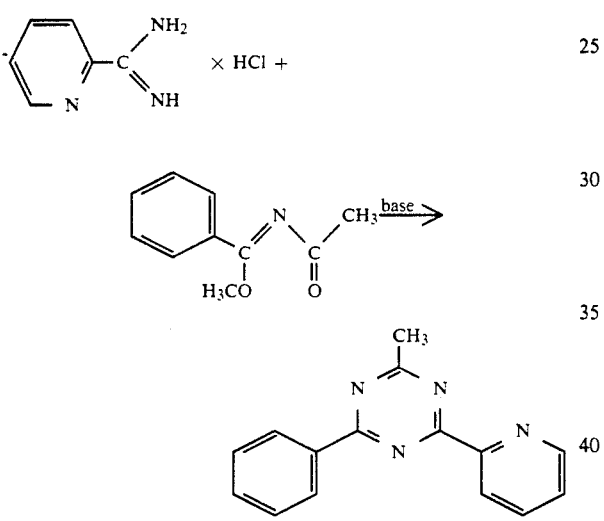

If, for example, 2-mercapto-4-(4-chlorophenyl)-6-(2-pyridyl)-1,3,5-triazine and Raney nickel are used as starting compounds, the course of the reaction of process (b) according to the invention can be represented by the following equation:

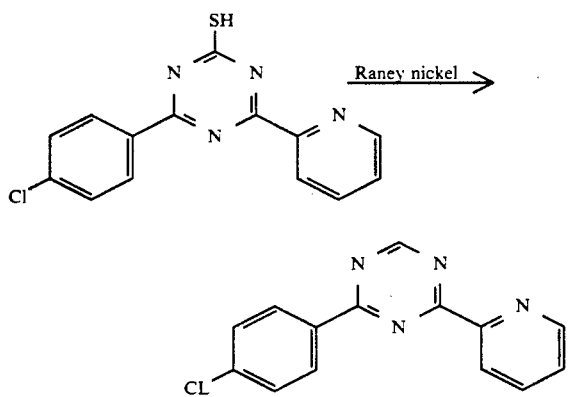

If, for example, 2-mercapto-4-(4-methylphenyl)-6-(2-pyridyl)-1,3,5-triazine and methyl iodide are used as starting compounds, the course of the reaction of process (c) according to the invention can be represented by the following equation:

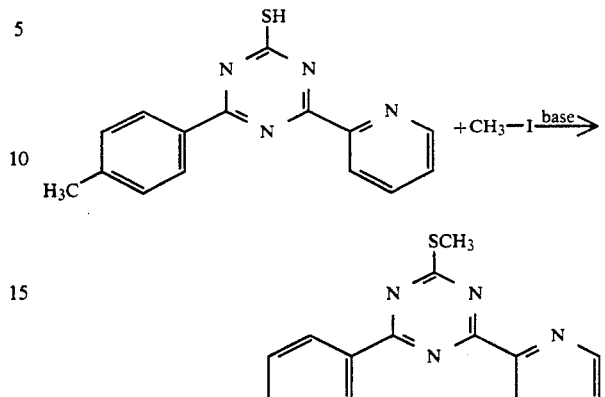

If, for example, 2-methylthio-4-(2-fluorophenyl)-6-(2-pyridyl)-1,3,5-triazine and methanol are used as starting compounds, the course of the reaction of process (d) according to the invention can be represented by the following equation:

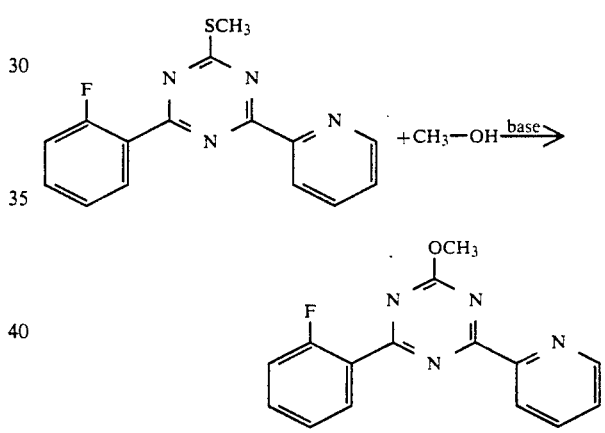

Formula (II) provides a definition of pyridylamidine or its acid addition salts, which is required as starting compound for carrying out process (a) according to the invention. In this formula (II) X preferably represents an anion of an inorganic mineral acid, particularly represents a halogen anion, such as a chloride anion, a bromide anion or an iodide anion or represents a hydrogensulfate anion or a hydrogencarbonate anion. Pyridylamidine or its acid addition salts of the formula (II), are known or can be prepared in analogues to known methods (cf., for example EP 259,139 or EP 270,362).

Formula (III) gives a general definition of the imidates furthermore required as starting substances for carrying out process (a) according to the invention. In this formula (III), $R^2$ preferably represents those radicals which have already been mentioned in connection with the description of the substances of the formula (I) according to the invention as being preferred for these substituents. $R^{1-1}$ preferably represents straight-chain or branched alkyl having 1 to 6, in particular 1 to 4, carbon atoms. $R^5$ preferably represents straight-chain or branched alkyl having 1 to 4 carbon atoms or represents phenyl.

The imidates of the formula (III) are known or can be obtained in analogy to known processes (cf., for example, Synthesis 1983, 483).

Formula (IV) provides a general definition of the mercapto-triazinylpyridines required as starting substances for carrying out processes (b) and (c) according to the invention. In this formula (IV), $R^2$ preferably represents those radicals which have already been mentioned in connection with the description of the substances of the formula (I) according to the invention as being preferred for these substituents. The mercapto-triazinylpyridines of the formula (IV) were hitherto unknown and are also a subject of the invention. They are obtained either when a 2-pyrdiylimidate of the formula (VII)

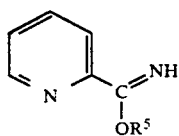

(VII)

in which $R^5$ represents alkyl or aryl, is initially reacted, in a first step, with benzoyl chlorides of the formula (VIII)

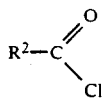

(VIII)

in which $R^2$ has the abovementioned meaning, if appropriate in the presence of a diluent such as, for example, toluene, and, if appropriate, in the presence of a reaction auxiliary such as, for example, triethylamine, at temperatures between $-20°$ C. and $+60°$ C., and the resulting N-acylated 2-pyridyl-imidates of the formula (IX)

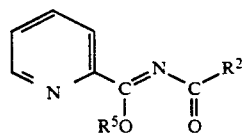

(IX)

in which $R^2$ and $R^5$ have the abovementioned meaning, are subsequently reacted with thiourea, if appropriate in the presence of a diluent such as, for example, methanol, or when pyridylamidine or its acid additions salts of the formula (II)

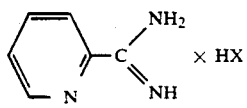

(II)

in which X represents the anion of an inorganic acid, is reacted with benzoyl isothiocyanates of the formula (X)

(X)

in which $R^2$ has the abovementioned meaning, if appropriate in the presence of a diluent such as, for example, a mixture of water and toluene and, if appropriate, in the presence of a reaction auxiliary such as, for example, sodium hydroxide, at temperatures between $-20°$ C. and $+60°$ C.

The resulting mercapto-triazinylpyridines of the formula (IV) can be further reacted directly in a so-called "one-pot process" according to process (b) or (c) according to the invention.

2-Pyridylimidates, of the formula (VII), are known or can be prepared in analogy to known methods (cf., for example, Chem. Letters 1975, 67–70).

Benzoyl chlorides of the formula (VIII) and benzoyl isothiocyanates of the formula (X) are generally known compounds of organic chemistry or can be obtained in analogy to generally known processes.

Formula (V) provides a general definition of the alkylating agents furthermore required as starting substances for carrying out process (c) according to the invention. In this formula (V), $R^3$ preferably represents straight-chain or branched alkyl having 1 to 6, in particular 1 to 4, carbon atoms. E represents a leaving radical customary in alkylating agents, preferably halogen, in particular chlorine, bromine or iodine, or in each case optionally substituted alkylsulphonyloxy, alkoxysulphonyloxy or arylsulphonyloxy such as, in particular, methanesulphonyloxy, trifluoromethanesulphonyloxy, methoxysulphonyloxy, ethoxysulphonyloxy or p-toluenesulphonyloxy. The alkylating agents of the formula (V) are generally known compounds of organic chemistry.

Formula (Ia) provides a general definition of the alkylthio-triazinylpyridines required as starting substances for carrying out process (d) according to the invention. In this formula (Ia), $R^2$ preferably represents those radicals which have already been mentioned in connection with the substances of the formula (I) according to the invention as being preferred for these substituents. $R^3$ preferably represents straight-chain or branched alkyl having 1 to 6, in particular 1 to 4, carbon atoms.

The alkylthio-triazinylpyridines of the formula (Ia) are compounds according to the invention and can be obtained with the aid of process (c) according to the invention.

Formula (VI) provides a general definition of the alcohols required as starting substances for carrying out process (d) according to the invention. In this formula (VI), $R^4$ preferably represents straight-chain or branched alkyl having 1 to 6, in particular 1 to 4, carbon atoms. The alcohols of the formula (VI) are generally known compounds of organic chemistry.

Diluents which are suitable for carrying out process (a) according to the invention are inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform or carbon tetrachloride; ethers such as diethyl ether, diisopropyl ether, dioxane, tetrahydrofuran or ethylene glycol dimethyl ether or ethylene glycol diethyl ether; ketones such as acetone or butanone or methyl isobutyl ketone; nitriles such as acetonitrile, propionitrile or benzonitrile; amides such as N,N-dimethylformamide, N,N-dimethylacetamide, N-methylformanilide, N-methylpyrrolidone or hexamethylphosphoric triamide; alcohols, such as methanol, ethanol, n- or i-propanol, or their mixtures with water, as well as pure water.

Process (a) according to the invention is preferably carried out in the presence of a suitable reaction auxiliary. Reaction auxiliaries which are suitable are all inorganic and organic bases which can customarily be used. The following are preferably used: hydrides, hydroxides, amides, alcoholates, carbonates or hydrogen carbonates of alkali metals such as, for example, sodium hydride, sodium amide, sodium hydroxide, sodium methylate, sodium ethylate, potassium t-butylate, sodium carbonate or sodium hydrogen carbonate, and also tertiary amines such as, for example, triethylamine, N,N-dimethylaniline, pyridine, N,N-dimethylaminopyridine, diazabicyclooctane (DABCO), diazabicyclononene (DBN) or diazabicycloundecene (DBU).

When carrying out process (a) according to the invention, the reaction temperatures can be varied within a substantial range. In general, the process is carried out at temperatures between 20° C. and 140° C, preferably at temperatures between 60° C. and 100° C.

Process (a) according to the invention is customarily carried out under atmospheric pressure. However, it is also possible to carry out the process under increased or reduced pressure.

For carrying out process (a) according to the invention, 1.0 to 3.0 mol, preferably 1.0 to 1.5 mol, of methyl imidate of the formula (III) and, if appropriate, 1.0 to 5.0 mol, preferably 1.0 to 2.5 mol, of base which is used as reaction auxiliary are generally employed per mole of pyridylamidine or an acid addition salt thereof of the formula (II). The reaction is carried out and the reaction products are worked up and isolated by generally customary methods (in this context, cf. also the Preparation Examples).

Suitable diluents for carrying out process (b) according to the invention are polar organic solvents which are miscible with water. These include, in particular, ethers such as dioxane, tetrahydrofuran or ethylene glycol dimethyl ether or ethylene glycol diethyl ether, or alcohols such as methanol, ethanol or n- or i-propanol, and their mixtures with water, or pure water.

If appropriate, process (b) according to the invention can be carried out in the presence of a suitable reaction auxiliary. A reaction auxiliary which is suitable is, in particular, aqueous ammonia.

When carrying out process (b) according to the invention, the reaction temperatures can be varied within a substantial range. In general, the process is carried out at temperatures between 0° C. and 150° C., preferably at temperatures between 40° C. and 100° C.

Process (b) according to the invention is customarily carried out under atmospheric pressure. However, it is also possible to carry out the process under increased pressure.

For carrying out process (b) according to the invention, 1.0 to 5.0 mol, preferably 1.0 to 2.5 mol, of Raney nickel and, if appropriate, 1.0 to 5.0 mol, preferably 1.0 to 2.5 mol, of reaction auxiliary are generally employed per mole of mercapto-triazinylpyridine of the formula (IV).

In a particularly preferred embodiment, the mercapto-triazinylpyridine of the formula (IV), which is used as starting compound, is prepared directly in the reaction vessel in a preceding reaction, and the resulting reaction mixture is subsequently further reacted directly with Raney nickel in a so-called "one-pot reaction" in accordance with process (b) according to the invention, without isolating the mercapto-triazinylpyridine of the formula (IV). The reaction is carried out and the reaction products are worked up and isolated by known processes (in this context, cf. also the Preparation Examples).

Suitable diluents for carrying out process (c) according to the invention are inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform or carbon tetrachloride; ethers such as diethyl ether, diisopropyl ether, dioxane, tetrahydrofuran or ethylene glycol dimethyl ether or ethylene glycol diethyl ether; ketones such as acetone or butanone or methyl isobutyl ketone; nitriles such as acetonitrile, propionitrile or benzonitrile; amides such as N,N-dimethylformamide, N,N-dimethylacetamide, N-methylformanilide, N-methylpyrrolidone or hexamethylphosphoric triamide, esters such as methyl acetate or ethyl acetate, or sulphoxides such as dimethyl sulphoxide, alcohols such as methanol, ethanol or n- or i-propanol, or their mixtures with water, and also pure water.

If appropriate, process (c) according to the invention can also be carried out in a two-phase system such as, for example, water/toluene or water/dichloromethane, if appropriate in the presence of a phase transfer catalyst. The following may be mentioned as examples of such catalysts: tetrabutylammonium iodide, tetrabutylammonium bromide, tetrabutylammonium chloride, tributyl-methylphosphonium bromide, trimethyl-$C_{13}/C_{15}$-alkylammonium chloride, trimethyl-$C_{13}/C_{15}$-alkylammonium bromide, dibenzyl-dimethylammoniummethylsulphate, dimethyl-$C_{12}/C_{14}$-alkyl-benzylammonium chloride, dimethyl-$C_{12}/C_{14}$-alkylbenzylammonium bromide, tetrabutylammonium hydroxide, 15-crown-5, 18-crown-6, triethylbenzylammonium chloride, trimethylbenzylammonium chloride or tris-[2-(2-methoxyethoxy)-ethyl]-amine.

Process (c) according to the invention is preferably carried out in the presence of a suitable reaction auxiliary. Reaction auxiliaries which are suitable are all inorganic and organic bases which can customarily be used. The following are preferably used: hydrides, hydroxides, amides, alcoholates, carbonates or hydrogen carbonates of alkali metals such as, for example, sodium hydride, sodium amide, sodium hydroxide, sodium methylate, sodium ethylate, potassium t butylate, sodium carbonate or sodium hydrogen carbonate, and also tertiary amines such as, for example, triethylamine, N,N-dimethylaniline, pyridine, N,N-dimethylaminopyridine, diazabicyclooctane (DABCO), diazabicyclononene (DBN) or diazabicycloundecene (DBU).

When carrying out process (c) according to the invention, the reaction temperatures can be varied within a substantial range. In general, the process is carried out at temperatures between −20° C. and +80° C., preferably at temperatures between 0° C. and +60° C.

For carrying out process (c) according to the invention, 1.0 to 3.0 mol, preferably 1.0 to 1.5 mol, of alkylating agent of the formula (V) and, if appropriate, 1.0 to 5.0 mol, preferably 1.0 to 2.5 mol, of base which is used as reaction auxiliary are generally employed per mole of mercapto-triazinylpyridine of the formula (IV). In a particularly preferred embodiment, the mercapto-triazinylpyridine of the formula (IV) which is used as starting compound is prepared directly in the reaction vessel in a preceding reaction, and the resulting reaction mixture is subsequently further reacted directly with the alkylating agent of the formula (V) in a so-called "one-pot reaction", without isolating the mercapto-triazinylpyridine of the formula (IV). The reaction is carried out and the reaction products are worked up and isolated by known processes (in this context, cf. also the Preparation Examples).

Suitable diluents for carrying out process (d) according to the invention are polar organic solvents which are miscible with water. These include, in particular, ethers such as dioxane, tetrahydrofuran or ethylene glycol dimethyl ether or ethylene glycol diethyl ether, or alcohols such as methanol, ethanol, n- or i-propanol, their mixtures with water or pure water.

It is particularly preferred to use a corresponding excess of alcohol of the formula (VI), which is used as reactant, simultaneously as the diluent.

Process (d) according to the invention is preferably carried out in the presence of a suitable reaction auxiliary. Reaction auxiliaries which are suitable are all inorganic and organic bases which can customarily be used. A reaction auxiliary which is particularly preferably used is an alkali metal alcoholate which corresponds to the alcohol of the formula (VI), which is used as reactant.

When carrying out process (d) according to the invention, the reaction temperatures can be varied within a substantial range. In general, the process is carried out at temperatures between 0° C. and 150° C., preferably at temperatures between 20° C. and 120° C.

For carrying out process (d) according to the invention, 1.0 to 20.0 mol, preferably 1.0 to 10.0 mol, of alcohol of the formula (VI) and, if appropriate, 1.0 to 2.0 mol, preferably 1.0 to 1.2 mol, of base which is used as reaction auxiliary are generally employed per mole of alkylthio-triazinylpyridine of the formula (Ia). The reaction is carried out and the reaction products are worked up and isolated by generally customary processes (in this context, cf. also the Preparation Examples).

The active compounds according to the invention have a powerful action against pests and can be employed in practise for combating undesired harmful organisms. The active compounds are suitable, for example, for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation: Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubensis;* Plasmopara species, such as, for example, *Plasmopara viticola;* Peronospora species, such as, for example, *Peronospora pisi* or *Peronospora brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *Pyrenophora graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae;* Pseudocercosporella species, such as, for example, *Pseudocercosporella herpotrichoides.* The good toleration, by plants, of the active compounds, at the concentrations required for combating plant diseases, permits treatment of above-ground parts of plants, of vegetative propagation stock and seeds, and of the soil.

In this context, the active compounds according to the invention can be employed with particular success for combating cereal diseases such as, for example, against the causative organism of leaf spot of barley (*Cochliobolus sativus*) or against the causative organism of leaf spot of wheat (*Leptosphaeria nodorum*) or against the causative organism of powdery mildew of cereals (*Erysiphe graminis*) or for combating diseases in fruit and vegetable growing such as, for example, against the causative organism of apple scab (*Venturia inaequalis*) or against the causative organism of powdery mildew of grapevine (*Uncinula necator*) or for combating rice diseases such as, for example, against the causative organism of rice blast disease (*Pyricularia oryzae*).

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene, alkylnaphthalenes, chlorinated aromatics or chlorinated aliphatic hydrocarbons, such as chlorobenzenes, chloroethylenes, or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenohydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, and in mixtures with fertilisers and growth regulators.

The active compounds can be used as such or in the form of their formulations or the use forms prepared therefrom such as ready-to-use solutions, suspensions, wettable powders, pastes, soluble powders, dusts and granules. They are used in the customary manner, for example by watering, spraying, atomising, scattering, dusting, foaming, brushing-on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001% by weight.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1

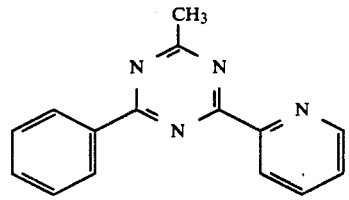

Process (a)

5.2 g (0.033 mol) of pyridine-2-carbamidine hydrochloride (cf., for example, EP 259,139 or EP 270,362), 5.8 g (0.033 mol) of methyl N-acetylbenzimidate and 8.4 g (0.039 mol) of a 20% strength sodium methylate solution in methanol are refluxed for 3 days in 60 ml of methanol, the mixture is subsequently cooled to room temperature and concentrated in vacuo, the residue is taken up in dichloromethane, the mixture is washed with water, dried over sodium sulphate and again concentrated in vacuo, and the residue is chromatographed over silica gel (eluent: n-hexane/acetone 7:3).

2.1 g (26% of theory) of 2-(2-pyridyl)-4-phenyl-6-methyl-1,3,5-triazine of melting point 97° C. are obtained.

Example 2

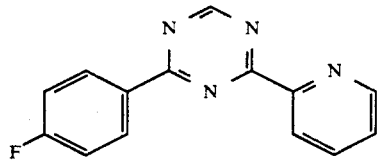

Process (b)

5 g of moist Raney nickel are added to a solution of 5.6 g (0.02 mol) of 2-(2-pyridyl)-4-(4-fluorophenyl)-6-mercapto-1,3,5-triazine in a mixture of 200 ml of ethanol, 200 ml of water and 50 ml of concentrated aqueous ammonia, and the mixture is refluxed for 6 hours. For working-up, the solution is filtered, the filtrate is concentrated to a volume of approx. 100 ml, and the precipitate which has separated out is filtered off with suction, taken up in methanol and filtered. The filtrate is concentrated, the residue is taken up in ethyl acetate, and the mixture is washed with water, dried over sodium sulphate and concentrated. The oily residue is brought to crystallisation by trituration with ether/petroleum ether.

0.5 g (10% of theory) of 2-(2-pyridyl)-4-(4-fluorophenyl)-1,3,5-triazine of melting point m.p. >180° C. (decomp.) is obtained.

Preparation of the Starting Compound

Example IV-1

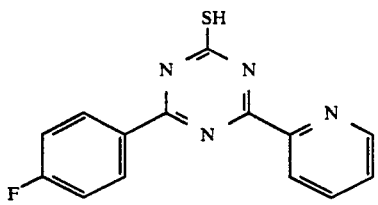

3.2 9 (0.02 mol) of pyridine-2-carbamidine hydrochloride are dissolved in 40 ml of water and covered with a layer of 80 ml of toluene. At the same time, 20 ml of 4 N sodium hydroxide solution and a solution of 3.6 g (0.02 mol) of 4-fluorobenzoyl isothiocyanate in 20 ml of toluene are added dropwise in each case with vigorous stirring in the course of 20 minutes, and stirring is subsequently continued at 20° C. for a further 18 hours. For working-up, an amount of methanol is added sufficient to produce a clear solution with two phases. The aqueous phase is separated off, brought to pH 5 using 2 N sulphuric acid, and precipitate which has separated out is filtered off with suction and dried.

4.0 g (70% of theory) of 2-(2-pyridyl)-4-(4-fluorophenyl)-6-mercapto-1,3,5-triazine of melting point >270° C. are obtained.

Example 3

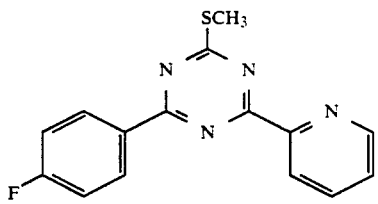

Process (c)

0.9 g (0.0066 mol) of methyl iodide is added to 1.7 g (0.006 mol) of 2-(2-pyridyl)-4-(4-fluorophenyl)-6-mercapto-1,3,5-triazine and 18 ml of 0.5 N-sodium hydroxide solution in 40 ml of ethanol, the mixture is subsequently stirred for 30 minutes at room temperature, and the resulting precipitate is then filtered off with suction and dried.

1.5 g (84% of theory) of 2-(2-pyridyl)-4-(4-fluorophenyl)-6-methylthio-1,3,5-triazine of melting point 158° C. are obtained.

Example 4

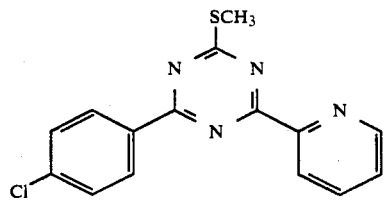

Process (c)—one-pot process 2.7 g (0.01 mol) of methyl N-(4-chlorobenzoyl)-pyridine-2-imidocarboxylate are added to a solution of 0.6 g (0.011 mol) of sodium methylate and 0.8 g (0.01 mol) of thiourea in 50 ml of methanol, the mixture is subsequently refluxed for 3 hours, 1.8 g (0.0125 mol) of methyl iodide are then added, and the mixture is stirred for a further 18 hours at room temperature. The precipitate which has separated out is filtered off with suction and dried.

0.4 g (13% of theory) of 2-(2-pyridyl)-4-(4-chlorophenyl)-6-methylthio-1,3,5-triazine of melting point 152° C. is obtained.

Example 5

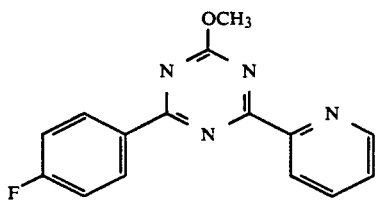

Process (d)

3.0 g (0.01 mol) of 2-(2-pyridyl)-4-(4-fluorophenyl)-6-methylthio-1,3,5-triazine are added to a solution of 0.5 g (0.01 mol) of sodium methylate in 100 ml of methanol, and the mixture is subsequently refluxed for 6 hours. For working-up, the reaction mixture is concentrated to approx. 20 ml and cooled, and the precipitate which has separated out is filtered off with suction and dried.

2.6 g (92% of theory) of 2-(2-pyridyl)-4-(4-fluorophenyl)-6-methoxy-1,3,5-triazine of melting point >270° C. are obtained.

The following substituted pyridyltriazines of the general formula (I)

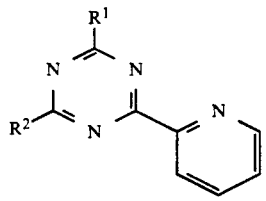

are obtained in a corresponding manner and following the general preparation instruction.

| Ex. No. | $R^1$ | $R^2$ | Melting point/°C. |
|---|---|---|---|
| 6 | $t\text{-}C_4H_9$ | ⟨phenyl⟩ | 71 |
| 7 | $CH_3$ | ⟨4-Cl-phenyl⟩ | 121 |
| 8 | $C_2H_5$ | ⟨4-Cl-phenyl⟩ | 112 |

-continued

| Ex. No. | R¹ | R² | Melting point/°C |
|---|---|---|---|
| 9 | $C_2H_5$ | phenyl | 80 |
| 10 | $n\text{-}C_3H_7$ | 4-chlorophenyl | 65 |
| 11 | $n\text{-}C_3H_7$ | phenyl | 102 |
| 12 | $-SCH_3$ | 4-methylphenyl | 165 |
| 13 | $-SCH_3$ | 3-chlorophenyl | 243 |
| 14 | $-OCH_3$ | 4-methylphenyl | >275 |

USE EXAMPLES

In the use examples which follow, the compounds listed below were employed as comparison substances:

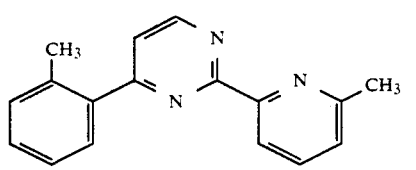

(A) 2-(6-methyl-2-pyridiyl)-4-(2-methylphenyl)-pyrimidine

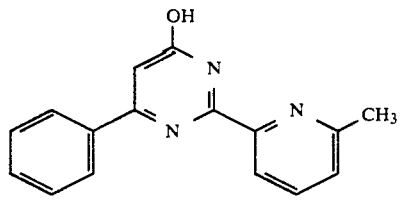

(B) 2-(6-methyl-2-pyridyl)-4-phenyl-6-hydroxy-pyrimidine

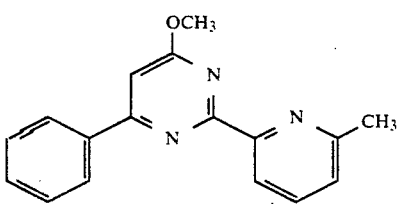

(C) 2-(6-methyl-2-pyridyl)-4-phenyl-6-methoxy-pyrimidine (all known from EP 270,362)

Example A

Venturia test (apple)/protective
Solvent: 4.7 parts by weight of acetone
Emulsifier: 0.3 part by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (Venturia inaequalis) and then remain for 1 day in an incubation cabin at 20° C. and 100% relative atmospheric humidity.

The plants are then placed in a greenhouse at 20° C. and a relative atmospheric humidity of about 70%.

Evaluation is effected 12 days after the inoculation.

A clearly superior activity compared with the prior art is shown in this test, for example, by the compounds of Preparation Examples: 1, 8 and 9.

Example B

*Leptosphaeria nodorum* Test (Wheat) Protective

Solvent: 100 parts by weight of dimethylformamide
Emulsifier: 0.25 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Leptosphaeria nodorum. The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is effected 10 days after the inoculation.

A clearly superior activity compared with the prior art is shown in this test, for example, by the compounds of Preparation Examples: 8 and 9.

Example C

*Cochliobolus sativus* Test (Barley)/Protective

Solvent: 100 parts by weight of dimethylformamide
Emulsifier: 0.25 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Cochliobolus sativus. The plants remain for 48 hours in an incubation cabin at 20° C. and 100% relative atmospheric humidity.

The plants are placed in a greenhouse at a temperature of about 20° C. and a relative atmospheric humidity of about 80%.

Evaluation is effected 7 days after the inoculation.

A clearly superior activity compared with the prior art is shown in this test, for example, by the compounds of Preparation Example: 10.

Example D

Uncinula test (Grapevine)/Protective

Solvent: 4.7 parts by weight of acetone
Emulsifier: 0.3 part by weight of alkylaryl polyglycol ether To produce a suitable preparation of active compound, 1 part by weight or active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus Uncinula necator.

The plants are subsequently placed in a greenhouse at 23° C. to 24° C. and a relative atmospheric humidity of about 75%.

Evaluation is effected 14 days after the inoculation.

A clearly superior activity compared with the prior art is shown in this test, for example, by the compounds of Preparation Examples: 4, 7, 8, 10 and 11.

We claim:

1. A substituted pyridyltriazine of the formula,

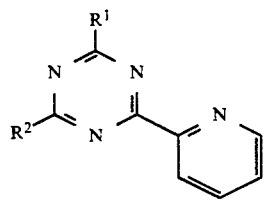

(I)

in which
R$^1$ represents hydrogen, straight-chain or branched alkyl having 1 to 6 carbon atoms, straight-chain or branched alkoxy having 1 to 6 carbon atoms, or straight-chain or branched alkylthio having 1 to 6 carbon atoms, and
R$^2$ represents phenyl which is optionally monosubstituted or polysubstituted by identical or different substituents selected from the group consisting of halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoxyiminoalkyl, each of which has 1 to 4 carbon atoms in the individual alkyl moieties, or phenyl which is optionally monosubstituted or polysubstituted by identical or different substituents selected from the group consisting of halogen and straight-chain or branched alkyl having 1 to 4 carbon atoms.

2. A substituted pyridyltriazine of the formula (I) according to claim 1, in which
R$^1$ represents hydrogen, straight-chain or branched alkyl having 1 to 4 carbon atoms, straight-chain or branched alkoxy having 1 to 4 carbon atoms or straight-chain or branched alkylthio having 1 to 4 carbon atoms, and
R$^2$ represents phenyl which is optionally monosubstituted to trisubstituted by identical or different substituents selected from the group consisting of fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl or phenyl which is optionally monosubstituted to trisubstituted by identical or different substituents selected from the group consisting of fluorine, chlorine, bromine, methyl and ethyl.

3. A substituted pyridyltriazine of the formula (I) according to claim 1, in which
R$^1$ represents hydrogen, methyl, ethyl, n- or i-propyl, n-, i-, s- or t-butyl, methoxy, ethoxy, methylthio or ethylthio, and
R$^2$ represents phenyl which is optionally monosubstituted or disubstituted by identical or different substituents and trifluoromethylthio.

4. A fungicidal composition comprising a fungicidally effective amount of at least one substituted pyridyltriazine according to claim 1 and a suitable extender.

5. A method of combating fungi comprising applying to such fungi or an environment thereof a fungicidally effective amount of at least one substituted pyridyltriazine according to claim 1.

6. A mercapto-substituted pyridyltriazine of the formula (IV)

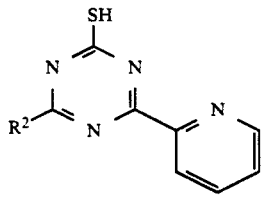

(IV)

in which R$^2$ represents phenyl which is optionally monosubstituted or polysubstituted by identical or different substituents selected from the group consisting of halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoxyiminoalkyl, each of which has 1 to 4 carbon atoms in the individual alkyl moieties, or phenyl which is optionally monosubstituted or polysubstituted by identical or different substituents selected from the group consisting of halogen and straight-chain or branched alkyl having 1 to 4 carbon atoms.

* * * * *